United States Patent [19]

Petrovich

[11] 4,378,350

[45] Mar. 29, 1983

[54] METHOD OF TREATING BACTERIAL, VIRAL OR PARASITIC DISEASES

[76] Inventor: Vojislav Petrovich, 1935 W. Schiller St., Chicago, Ill. 60622

[21] Appl. No.: 425,486

[22] Filed: Sep. 28, 1982

Related U.S. Application Data

[63] Continuation-in-part of Ser. No. 187,584, Sep. 15, 1980, abandoned, and a continuation-in-part of Ser. No. 187,585, Sep. 15, 1980, abandoned, and a continuation-in-part of Ser. No. 196,862, Sep. 14, 1980, abandoned, and a continuation-in-part of Ser. No. 233,036, Feb. 9, 1981, abandoned, and a continuation-in-part of Ser. No. 233,037, Feb. 9, 1981, abandoned, and a continuation-in-part of Ser. No. 287,428, Jul. 27, 1981, abandoned, and a continuation-in-part of Ser. No. 288,302, Jul. 30, 1981, abandoned, and a continuation-in-part of Ser. No. 288,304, Jul. 30, 1981, abandoned, and a continuation-in-part of Ser. No. 294,849, Aug. 21, 1981, abandoned, and a continuation-in-part of Ser. No. 294,850, Aug. 21, 1981, abandoned, and a continuation-in-part of Ser. No. 298,178, Aug. 31, 1981, abandoned, and a continuation-in-part of Ser. No. 400,590, Jul. 22, 1982, abandoned, and a continuation-in-part of Ser. No. 400,591, Jul. 22, 1982, abandoned, and a continuation-in-part of Ser. No. 400,592, Jul. 22, 1982, abandoned.

[51] Int. Cl.³ .................... A61K 33/04; A61K 31/19; A61K 31/205

[52] U.S. Cl. .................... 424/164; 424/317; 424/319

[58] Field of Search .................... 424/167, 317, 319

[56] References Cited

U.S. PATENT DOCUMENTS

2,917,429 12/1959 Scott .
3,167,471 1/1965 Kovacs .
3,846,459 11/1974 Stapfer .
3,976,781 8/1976 Kalopissis .
4,107,330 8/1978 Sheffner .
4,148,885 4/1979 Renonx .
4,151,301 4/1979 Kalopissis .

FOREIGN PATENT DOCUMENTS

2917790 11/1979 Fed. Rep. of Germany .

*Primary Examiner*—Anna P. Fagelson

[57] ABSTRACT

The invention relates to a therapeutic mixture for treating bacterial and viral infections and exterminating parasites in human and animal host; comprises a therapeutically effective mixture consisting of mercaptolactic sodium salt, and dipotassium hydrosulfate, which in conjunction perform after injection a permanent reducing action liberating charged hydrogen, and charged thiolactic radical, which are biologically active neutralizing and transforming bacteria and viruses, and kill the parasites.

3 Claims, No Drawings

METHOD OF TREATING BACTERIAL, VIRAL OR PARASITIC DISEASES

This application is a continuation in part of the applications:

Ser. No. 187,584, filed Sept. 15, 1980, Ser. No. 187,585, filed Sept. 15, 1980, Ser. No. 196,862, filed Sept. 14, 1980, Ser. No. 233,036, filed Feb. 9, 1981, Ser. No. 233,037, filed Feb. 9, 1981, Ser. No. 287,428, filed July 27, 1981, Ser. No. 288,302, filed July 30, 1981, Ser. No. 288,304 filed July 30, 1981, Ser. No. 294,849, filed Aug. 21, 1981, Ser. No. 294,850, filed Aug. 21, 1981, Ser. No. 298,178, filed Aug. 31, 1981, Ser. No. 400,590 filed July 22, 1982, Ser. No. 400,591, filed July 22, 1982, Ser. No. 400,592, filed July 22, 1982, which are abandoned.

This invention relates to a therapeutic action of reducing media for controlling bacterial and viral infections and parasitic infestion in human and animal host by applying a therapeutic mixture consisting of mercaptolactic sodium salt and dipotassium hydrosulfate. Said mercaptolactic sodium salt in conjunction with reducing dipotassium hydrosulfate perform after injection a permanent reducing action liberating charged hydrogen, and charged thiolactic radical which are biologically active which is manifested by neutralizing, or transforming the bacteria and viruses to nonagressive macromolecules, while killing parasites.

The mechanism of action of mercaptolactic sodium salt in conjunction with dipotassium hydrosulfate unfolds a reducing process in a reducing medium which consequently contributes to the development of nascent and bilogically active charged hydrogen, as well as the development of nascent charged thiolactic radical. The supposedly antibacterial and antiviral action is accomplished by the integration of charged hydrogen and charged thiolactic radical derived from reduced mercaptolactic sodium salt, which complete the bacterial and viral nucleoproteides and thus neutralize their activity, while charged thiolactic radical which being unstable, when unite to dithiodilactic acid in the presence of parasites, said dithiodilactic acid is poisonous to parasites and thus kill them.

The regenerative reversible process in the formation of thiolactic acid and mercaptolactic acid to release the active charged hydrogen develops by inherent oxidizing process and the reducing action of dipotassium hydrosulfate. The reverse process is manifested in permanently reducing charged thiolactic radical to mercaptolactic acid as long as it is of disposable hydrogen from dipotassium hydrosulfate reducing action developed by hydrolysis. Each oxidation and reduction is sustained in reversible conditions, which is very important timely and biologically.

Reversible oxidation and reduction of mercaptolactic sodium salt makes feasible that the combination of said compounds with mild reducing agents such as dipotassium hydrosulfate, partake in the formation of biologically active hydrogen, i.e., charged hydrogen and charged thiolactic radical. Combining charged hydrogen and charged thiolactic radical follows de-oxidation and neutralisation of bacteria and viruses unsaturated macromolecules, while the parasites under such conditions are killed. Thus the nascent charged hydrogen, and nascent charged thiolactic radical by their reactivity promote the antibacterial and antiviral action, as well as provoke the killing of parasites, which is the essence of this invention.

The charged hydrogen and the charged thiolactic radical are capable to bind unsaturated compounds on which behavior is based antibacterial and antiviral action of this invention. For, macromolecules undoubtedly have no homogeneous charge distribution, which should provide potential sites for trapping displaced electrons or binding holes in addition to those sites associated with lettuce imperfection.

The advantage of disclosed pharmacologically active reducing media with charged hydrogen radical, charged thiolactic radical, resides in non-toxic quality of disclosed process. No side effects can be expected by application of simple mercaptolactic sodium salt, aided by dipotassium hydrosulfate with reducing capabilities by evolving disposable hydrogen. The thiolactic radical is of short duration, because emitting charged hydrogen. Therefore, no toxic action may be incurred anyhow. The mercaptolactic acid is to some extent toxic, if used with dipotassium hydrosulfate of which the dose may be several times bigger because of acting redoxy process. The said thiolactic acid being unstable in neutral and weakly alkaline media as is the blood serum oxidizes to disulfide diacid by emitting hydrogen. The presence of dipotassium hydrosulfate prevents the formation of disulfide, as well as the presence of parasites, which is always present in said process but is of short duration. The dipotassium hydrosulfate oxidizes to dipotassium sulfate by the way of hydrolysis emitting two charged hydrogen. Because the process of oxidation-reduction evolves in blood serum the presence of dipotassium hydrosulfate diminishes the needed presence of mercaptolactic acid for several times as pharmacologically needed to produce and emit charged hydrogen for biologic synthesis, whereas the charged thiolactic radical is permanently and succeedingly incorporated in nucleoproteides of bacteria and viruses and/or in killing parasites until complete exhaustion and consummation. Thus, no toxic action can be incurred, while dipotassium sulfate the only unassimilable product is eliminated from the organism.

Explaining the possible mechanism of action in controlling bacteria, viruses, and parasites it was observed that all purulent processes of chronic character, suppurations, pustules, furuncles, various abcesses, various eczemas, purulent staphlococcal infections, streptococcal and other bacterial infections, mastitis, actinomycosis, actinobacillosis, mycosis, mycetes, endometritis may be healed with therapeutical mixture of this invention. Furthermore, myxovirus infection, mixomatosis and the like infections are successfully controlled. Of the parasitic diseases, the protozoan diseases, parasites of the type ixodides, teliasis, the parasitic sickness of eye conjunctives in bovine, mange in bovine and all animals are successfully exterminated with therapeutical mixture of this invention.

The application in human is fulfilled with one injection at intervals of one or two days. The applications are fulfilled by priority intravenous, but may be applied also intramuscular. If applied intramuscular then the application is made in two places, i.e, in the left and right thigh. When applied intramuscular certain irritation may be felt, otherwise no other consequences may appear. The dose may be increased until 12 injection in the course of healing. All is worked slowly. The intervals may be longer, which depends on the case. In cases of internal purulent processes and inflamations with suppurations and inner pustule the application must be gradual because the inner pustule may close and form a scar, which may require an operation.

The standard combination of healing ingredients for human use is 200 mg of dry mercaptolactic sodium salt, and 800 mg of dry dipotassium hydrosulfate, both dissolved before injection in 10 ccm distilled water per 24 hour period.

The standard combination of healing ingredients for animal use is stronger for big animals and the amount varies depending of the net weight of animal. Thus, for each 50 kg net weight of animal 1 ccm of 100 mg of dry mercaptolactic sodium salt, and 300 mg of dry dipotassium hydrosulfate, both dissolved before injection in 1 ccm distilled water per 24 hour period.

What is claimed is:

1. A method for treating a human or animal host infected with bacteria and viruses or infested with parasites which comprises; Administering to said host a pharmaceutical composition comprising, mercaptolactic acid or its sodium salt and dipotassium hydrosulfate in amount effective to give a reducing action in vivo after injection liberating charged hydrogen and charged thiolactic radical for neturalizing bacteria and viruses and killing parasites.

2. The method of claim 1, where the pharmaceutical composition comprises 100 to 200 mg of dry mercaptolactic acid or its sodium salt and 300 to 800 mg of dry dipotassium hydrosulfate both dissolved in 1 to 10 ccm distilled water, which is injected intravenously or intramuscularly in the host in need of such treatment per 24 hour period.

3. The method of claim 1, for treating said human or animal host infected with bacteria or viruses, or infested with parasites which further comprises:
   (a) treating said human or animal host in need of said treatment with repeated administration by intravenous injection or intramuscular injection in two sites with an antibacterial, antiviral and antiparasite effective amount therefore of a pharmaceutical mixture containing as active ingredients mercaptolactic sodium salt and dipotassium hydrosulfate;
   (b) the dosage range per 24 hour period of the mixture in adult human patient being about 200 mg og dry mercaptolactic sodium salt, and 800 mg of dry dipotassium hydrosulfate, both dissolved before injection in 10 ccm distilled water; and
   (c) the dosage range per 24 hour period of the mixture for grown animal being about 1 ccm for each 50 kg net weight of the animal, which mixture contains 100 mg of dry mercaptolactic sodium salt, and 300 mg of dry dipotassium hydrosulfate, both dissolved before injection in 1 ccm distilled water.

* * * * *